United States Patent
Wagner

(10) Patent No.: US 8,376,738 B2
(45) Date of Patent: Feb. 19, 2013

(54) UNIVERSAL IMPRESSION TRAYS AND METHOD OF USE

(75) Inventor: Stephen Wagner, Albuquerque, NM (US)

(73) Assignee: Big Jaw Bone, LLC, Albuquerque, NM (US)

(*) Notice: Subject to any disclaimer, the term of this patent is extended or adjusted under 35 U.S.C. 154(b) by 411 days.

(21) Appl. No.: 12/144,787

(22) Filed: Jun. 24, 2008

(65) Prior Publication Data

US 2008/0254406 A1 Oct. 16, 2008

Related U.S. Application Data

(63) Continuation-in-part of application No. 11/256,519, filed on Oct. 20, 2005, now abandoned.

(60) Provisional application No. 60/621,026, filed on Oct. 20, 2004.

(51) Int. Cl.
*A61C 3/00* (2006.01)
(52) U.S. Cl. .................................................. 433/6
(58) Field of Classification Search .......... 433/6, 34–48; 128/861, 862
See application file for complete search history.

(56) References Cited

U.S. PATENT DOCUMENTS

| | | |
|---|---|---|
| 55,465 A | 6/1866 | Buttles |
| 90,802 A | 6/1869 | Wuestenberg |
| 111,429 A | 1/1871 | Boughton |
| 310,407 A | 1/1885 | Garner |
| 347,976 A | 8/1886 | Starr |
| 415,594 A | 11/1889 | Weirich |
| 1,503,580 A | 8/1924 | Epstein |
| 1,563,955 A | 12/1925 | Barton |
| 1,763,553 A | 6/1930 | Dennis |
| 3,234,942 A | 2/1966 | Simor |
| 3,890,711 A | 6/1975 | Burns |
| 4,259,074 A | 3/1981 | Link |
| 4,445,854 A * | 5/1984 | Bekey et al. ............. 433/37 |
| 4,530,662 A | 7/1985 | Anderson et al. |
| D289,795 S | 5/1987 | Anderson |
| 4,768,951 A | 9/1988 | Abiru et al. |
| 5,112,225 A | 5/1992 | Diesso |
| 5,554,024 A * | 9/1996 | Ueda ....................... 433/37 |
| 6,196,840 B1 * | 3/2001 | Zentz et al. ............. 433/71 |
| 7,305,990 B2 | 12/2007 | Mathias |
| 2005/0034733 A1* | 2/2005 | Liddle et al. ............ 128/859 |
| 2005/0106529 A1* | 5/2005 | Abolfathi et al. ........ 433/41 |
| 2006/0105289 A1 | 5/2006 | Wagner |
| 2006/0183080 A1* | 8/2006 | Nosov et al. ............ 433/215 |

* cited by examiner

*Primary Examiner* — Sunil K Singh
(74) *Attorney, Agent, or Firm* — Samantha A. Updegraff; Deborah A. Peacock; Peacock Myers, P.C.

(57) ABSTRACT

A universal impression tray can be reshaped shortened or lengthened allowing a clinician the ability to use one tray in any clinical situation. The tray itself can be used with patients requiring complete removable dentures, root supported and implant-supported overdentures and in some selected dentate cases. The tray can be infinitely modified allowing total control by the clinician. Trays in accordance with features of the present invention are made of a material composition including thermoplastic resin and thermochromic pigment. The material composition softens and changes color in warm water but tends to hold its shape until manipulated by the dentist. The thermoplastic resin portion of the tray can include polycaprolactone resin, styrene resin and dental modeling compound and can vary for specific uses to roughly 50% polycaprolactone /styrene resin and 50% dental modeling compound. Thermochromic pigment can represent up to 5% of the overall material composition of a tray.

10 Claims, 10 Drawing Sheets

UNIVERSAL IMPRESSION TRAYS AND METHOD OF USE

PRIORITY AND CROSS-REFERENCE TO RELATED APPLICATION

This patent application is being filed as a Continuation-in-part and claims priority to U.S. Non-provisional patent application Ser. No. 11/256,519, filed Oct. 20, 2005, now abandoned and which further claims priority under 35 U.S.C. §119(e) to provisional patent application Ser. No. 60/621,026 filed Oct. 20, 2004, the disclosure of which is incorporated herein by reference.

FIELD OF THE INVENTION

The present invention is generally related to impression making trays. More particularly, the present invention is related to a universal impression tray that enables a clinician to use only one maxillary and or one mandibular impression tray in any clinical situation where impressions are required.

BACKGROUND

Many dental procedures require the dentist to form an impression of patients' teeth, either alone or in conjunction with the gums and vestibular anatomy. This impression typically is either used directly by the dentist to analyze the patient's mouth structure or is used to form a plaster replica of the patient's teeth, gums, and vestibule. Such impressions are typically used to produce dental replacement components and dental assemblies such as crowns, teeth, bridgework, dentures and other oral prostheses.

Dental impression trays for obtaining an impression of a patient's dentition are well known. Such trays generally include tray portions anatomically contoured to fit at least a part of a patient's upper and/or lower oral anatomy, of which an impression is to be obtained. An appropriate impression material is placed in the tray and inserted in the mouth. After the impression material sets, it is used as a mold, into which plaster or dental stone can be poured which upon setting forms a model of the patient's oral anatomy. In addition, the set impression material may also be used directly as a mold for other purposes such as the fabrication of temporary restorations, the process of teeth whitening etc.

Dentists use trays to carry impression material to the mouth and to support the moldable material intra-orally until it cures. The design of the tray depends on the size and shape of the area to be recorded. Tray sets typically include variably-sized upper and lower troughs, each filled with impression material such as a settable material. The upper impression corresponds to an impression section of maxilla, the lower impression corresponds to a complimentary section of mandible, and the two complimentary impressions jointly provide an impression of the bite relationship of mandible to maxilla.

Metal trays are typically used for the above-mentioned procedures. Metal trays are expensive. They require cleaning and sterilization before reuse, which is inconvenient. In the process of obtaining any impression, called the modeling process, dental trays to contain the impression materials are used, and such dental impression trays are generally classified into ready-made (stock) trays and customized trays. In order to obtain more exact impression, customized trays fitted on an individual are manufactured from the model made by using the ready-made trays. So, ready-made trays could be regarded as one of the most basic apparatus for manufacturing an exact restoration. The arch has the shape of a horse hoof formed by person's teeth and alveolar bones, and its size and shape differs from person to person. A set of ready-made dental impression trays usually comprises at least 4 maxillary trays (small, medium, large and extra large) and at least 3 mandibular trays (small, medium and large). However, these conventional ready-made trays are so complex that even an expert has some difficulty in selecting and classifying them, and furthermore, there are some cases that none of such ready-made trays fits an individual. It is, therefore, difficult to obtain an exact impression through conventional ready-made trays.

Current disposable trays are inexpensive, which gives them the convenience of disposability. However, their flexibility and plastic memory can cause intra-oral distortions in the impression. The lack of complete rigidity in a plastic tray can create a "springback" distortion transfer from the tray to the impression material on release of pressure to the tray sides, which is inadvertently applied by hard- and soft-tissue interferences at some point during the impression-making process. For example, pressure can be generated by the tongue, by occlusal forces pushing material against the tray wall, by the cheeks, or by tray impingement of gingival tissues, alveolar ridge, retromolar pad, tuberosity and teeth. This pressure flexes the tray while the impression material sets, causing inaccuracies in the impression when the distorted tray attempts to return to its original shape upon removal from the mouth. An impression in a flexible frame can also be distorted by forces applied to remove the tray from the patient's mouth or during routine laboratory handling. These inaccuracies are then transferred to the master cast when it is made in the dental laboratory.

The use of thermoplastics in the field of dentistry is known. Conventionally, hardened or semi-hardened thermoplastics are used in the making of dental impressions, for example. Thermoplastics are also used as material to build up regions of castings that serve as the basis for making dentures. In order to melt or soften thermoplastics in the conventional dental office or laboratory, a dedicated water bath, which may be a so-called crock pot, such as found in the domestic kitchens, has been used to soften the thermoplastic. Alternatively, it has been known to heat up a cup of water in a microwave oven to a temperature of 150.degree. F. or more, and then carry the hot cup of water into the room where the dentist or technician is working the thermoplastic material. Currently in the dental field thermoplastic is typically used in the form of pre-formed wafers, such as so-called TEMP-TABS™, which are heated in use. There is also known thermoplastic which is incorporated in a triple tray or dental impression tray, such as a so-called THERMO-TRAY™. Both the TEMP-TABS™ and the THERMO-TRAY™ must be softened in hot water, as discussed above. This heating in the dental office not only leads to the problems discussed above, but if the thermoplastic is improperly overheated, it may develop undesirable bubbles. Further, the TEMP-TABS™ are very costly and, even if a relatively small quantity of TEMP-TABS™ is required for a procedure, such may be cost prohibitive.

Unformed thermoplastic is a relatively inexpensive material. Needless to say, such prior art devices and methods of heating and using heated thermoplastic material are impractical, if not unwieldy.

What is needed is a new tray system that will fit any patient during any clinical situation using any impression making technique that is required. What is also needed is a tray system that is universal and easy to use by clinicians.

SUMMARY

In accordance with features of the present invention, a universal impression tray will now be described that is designed to produce high-quality final impressions in one clinical visit.

In accordance with features of the present invention, a universal edentulous impression tray is disclosed that is comprised of a thermoplastic resin that softens and changes its color in warm water but tends to hold its shape until manipulated.

In accordance with another feature of the present invention, the tray includes a main body including a trench, interior wall and exterior wall; and a handle integrated with the front of the main body, wherein the tray can be reshaped shortened or lengthened allowing a clinician the ability to use one tray in any clinical situation.

In accordance with a method of using the invention, a set of universal trays (one maxillary tray and one mandibular tray) are accessed from clinic stock and are compared with the maxilla or mandible regions of a patient's mouth. After the comparison the tray is heated to at least 140 degrees Fahrenheit so that excess material can be added or removed to the tray as needed to adapt it to the entire maxilla or mandible region of the patient's mouth. Tray heating is indicated by a change in tray color, which is enabled by a thermochromic pigment incorporated into the tray material. Surfaces of the tray can then be smoothed out after material is added or removed prior to reinstalling the tray into the patient's mouth for further adjustment. A clinician can determine if the adjusted tray fits within the patient's mouth along the maxilla or mandible regions by determining whether the tray requires more or less material; and if the tray requires the addition or removal of material, the tray is reheated and then excess material can be again added/removed and the tray smoothed out until a match is obtained. The tray is then reheated and chilled during manipulation and while the tray is being adapted to the patient's maxilla or mandible regions. This process is repeated until a satisfactory fit is achieved. Once a fit is achieved, impression material is added to a satisfactory fitting tray, and the tray placed in the patient's mouth so that an impression of the maxilla or mandible regions can be achieved.

In accordance with additional features of the present invention a universal maxillary and single mandibular tray can be easily reshaped shortened or lengthened allowing a clinician the ability to use one tray in any clinical situation. The tray itself can be used with patients requiring complete removable dentures, root supported and implant-supported overdentures and in some selected dentate cases. The tray can be infinitely modified allowing total control by the clinician. The tray can be easily adapted in the chair side or in the laboratory and formed in the patient's mouth. Any impression-making philosophy is supported by this impression tray system. For the first time the dentist is able to adapt a single tray to fit his or her unique impression making technique rather than compromising technique to fit the limitations of inflexible trays that cannot be easily modified. Of course, a tray in accordance with teachings of the present invention can be quickly adapted to patients with maxillofacial defects.

The present invention accomplishes superior results over the prior dental impression technology in two ways. Trays in accordance with features of the present invention are made of a thermoplastic resin including thermochromic pigment that softens and changes color in warm water but tends to hold its shape until manipulated by the dentist. The resin is comprised of polycaprolactone resin, styrene resin and dental modeling compound. The proportions of thermoplastic resin portion of the tray can vary for specific uses but are ideally 50% polycaprolactone/styrene resin and 50% dental modeling compound. Very little thermochromic pigment is required to indicate temperature change in the tray. Less than 5% of the trays composition can include thermochromic pigment to accomplish a thermochromatic effect during tray heating.

DETAILED DESCRIPTION OF THE INVENTION

In accordance with features of the present invention, a single set of trays can be used for maxilla or mandible impression making procedures. The preformed, universal trays of present invention accomplish superior results over the prior dental impression technology in two ways. Maxilla and mandible trays in accordance with features of the present invention are made of a thermoplastic resin that softens in warm water but tends to hold its shape until manipulated by the dentist.

Figure 1:
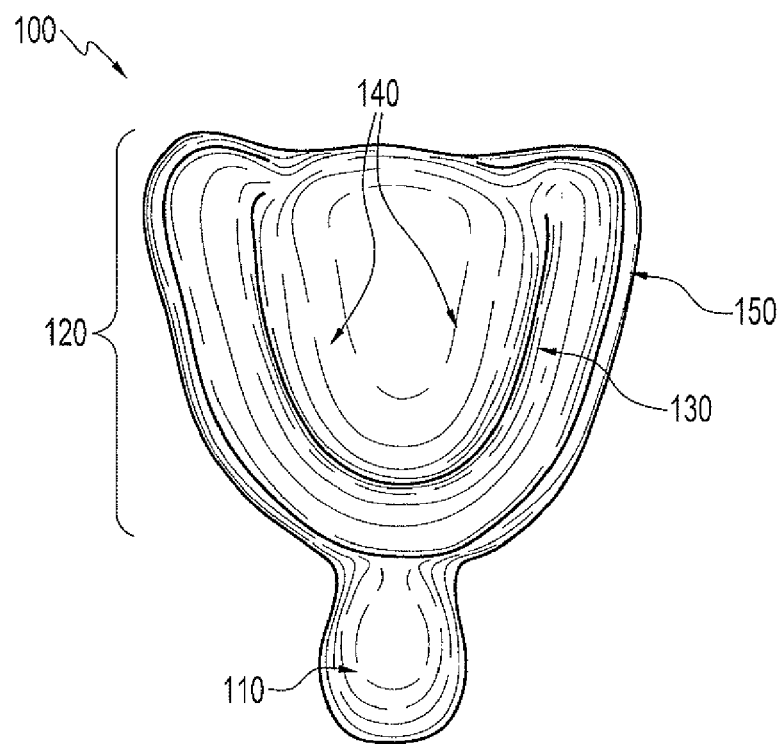
FIG. 1 illustrates a top view of a maxilla tray in accordance with features of the present invention.

Referring to FIG. 1, a top view of a maxilla tray 100 in accordance with features of the present invention is shown. The tray 100 is shown with a handle 110 and a main body 120 that is formed as an arch or as the shape of a horse hoof. The main body 120 is further formed by person's teeth and alveolar bones during use when they are received within the trench 130 also formed along the main body in the form of an arch, but including interior and exterior walls, labeled 140 and 150 respectively.

The material composition of the tray 100 includes a uniform thermoplastic resin-based material and a thermochromic pigment. The thermoplastic resin can include polycaprolactone resin, styrene resin and dental modeling compound. The thermoplastic material proportion of the tray is the dominant material in the tray and can vary for specific uses, but can be roughly 50% polycaprolactone/styrene resin and 50% dental modeling compound. The thermochromic pigment material is the less dominant material and can comprise up to 5% of the overall material composition of the tray.

By incorporating a thermochromic pigment, the tray can change color when warmed and allows the practitioner to selectively modify the tray in the patient's mouth and create a custom tray prior to making a final impression. In actual test, tray material incorporating thermochromic pigment changes color from blue to tan when heated in warm water, which then indicates that the tray material is heated and is therefore pliable and can be easily shaped to the contours of the patient's edentulous ridge. The new contours can then be retained in the tray when cooled and permits the making of an accurate final impression of the edentulous ridge.

Figure 2:
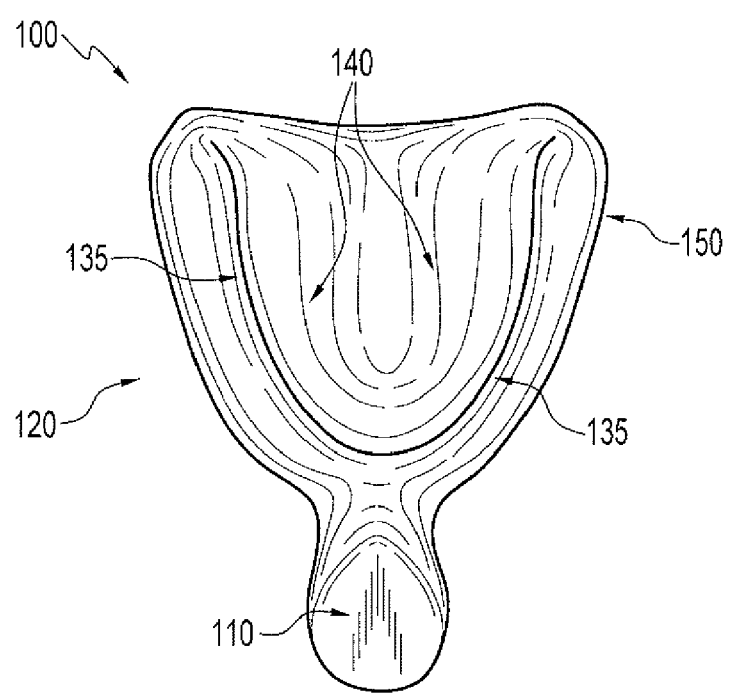
FIG. 2 illustrates a bottom view of the maxilla tray in FIG. 1.

Referring to FIG. 2, a bottom view of the maxilla tray 100 is shown. Also shown in FIG. 2 is the outer surface detail of the trench wherein a ridgeline 135 generally follows the shape of a horseshoe along the bottom surface, opposite the trench 130 shown in FIG. 1.

Figure 3:
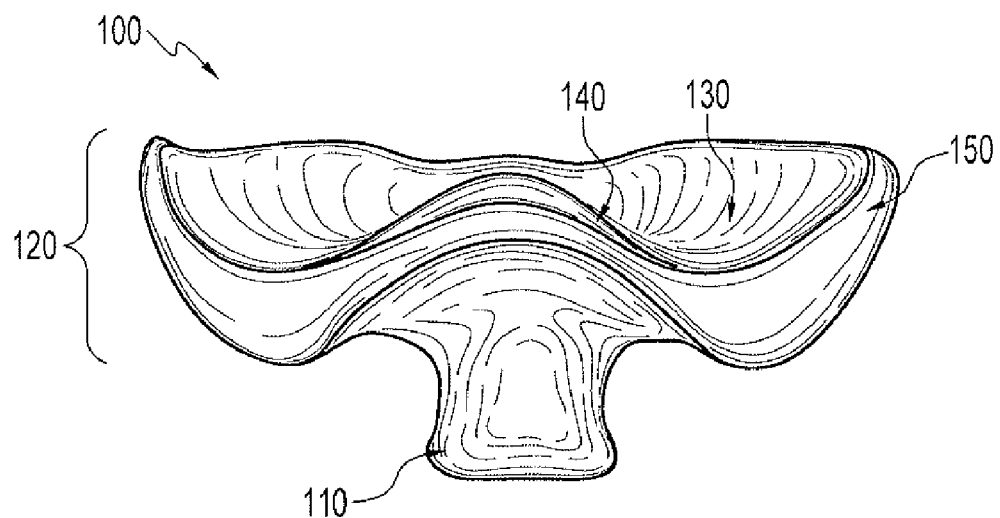
FIG. 3 illustrates a rear view of the maxilla tray in FIG. 1, shown with more detail of the trench as formed by the interior wall and exterior wall.

Referring to FIG. 3, a back view of the maxilla tray 100 is shown with more detail of the trench 130 as formed by the interior wall 140 and exterior wall 150. The handle 110 is also shown in FIG. 3 in lowered relation to the main body 120.

Figure 4:
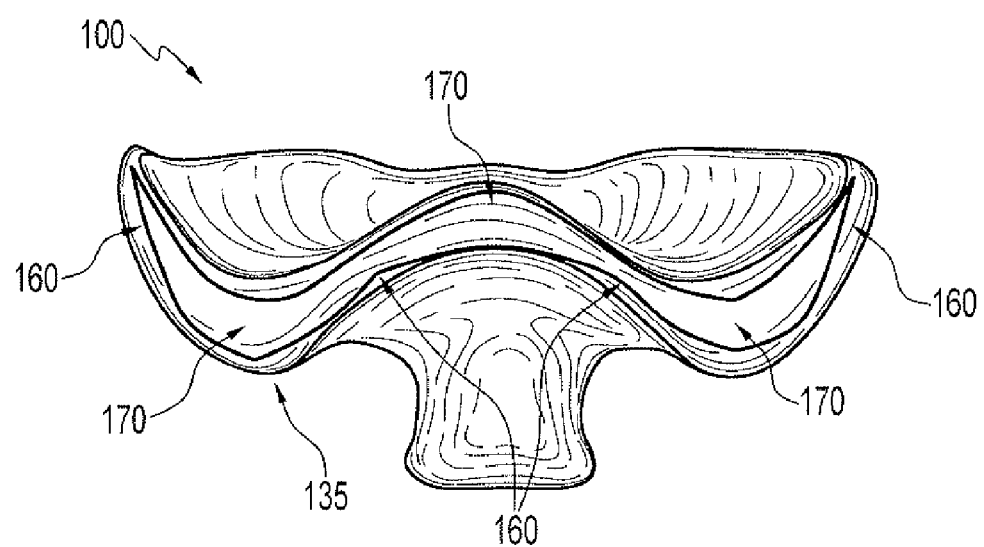
FIG. 4 illustrates a cross sectional rear view of the maxilla tray in FIG. 1.

Referring to FIG. 4, a cross sectional back view of the maxilla tray 100 is shown with lines to illustrate various thick and thin regions along the trench and wall area of the tray. Thin areas enable easy manipulation of the tray, while thicker areas help maintain the trays integrity. The cross sectional view best illustrates the various thicknesses embodied within the tray's main body 120. The thick regions 170 enable technicians/dentists to maintain the trays integrity, including its basic horseshoe shape. The thinner regions 160 are located in areas along the tray that traditionally cause most problems during use, including patient discomfort, difficulty achieving a snug fit of the tray with the patients teeth, gums and mouth.

Figure 5:
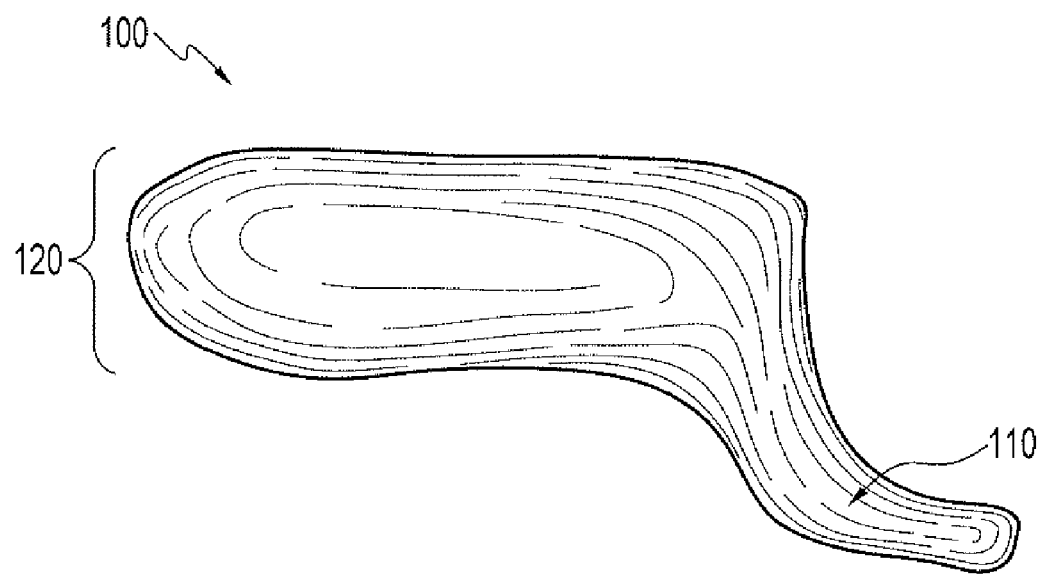
FIG. 5 illustrates a side view of the maxilla tray shown in FIG. 1.

Referring to FIG. 5, a side view of the maxilla tray 100 is shown. The main body 120 and handle 110 are shown. The side view of the main body 120 also shows the exterior wall 140.

Figure 6:
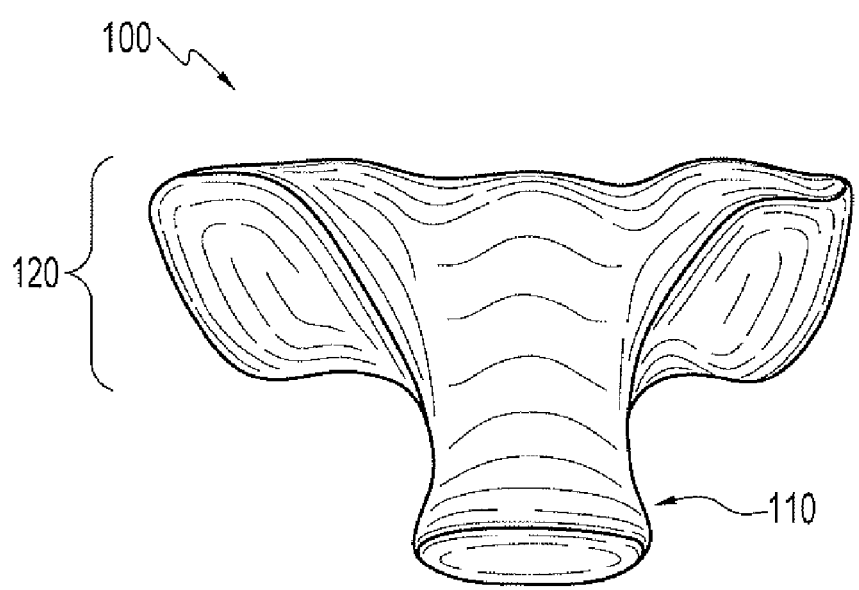
FIG. 6 illustrates a front view of the maxilla tray shown in FIG. 1.

Referring to FIG. 6, a front view of the maxilla tray 100 is shown. The main body 120 and handle 110 are also shown in the back view of FIG. 6.

Figure 7:
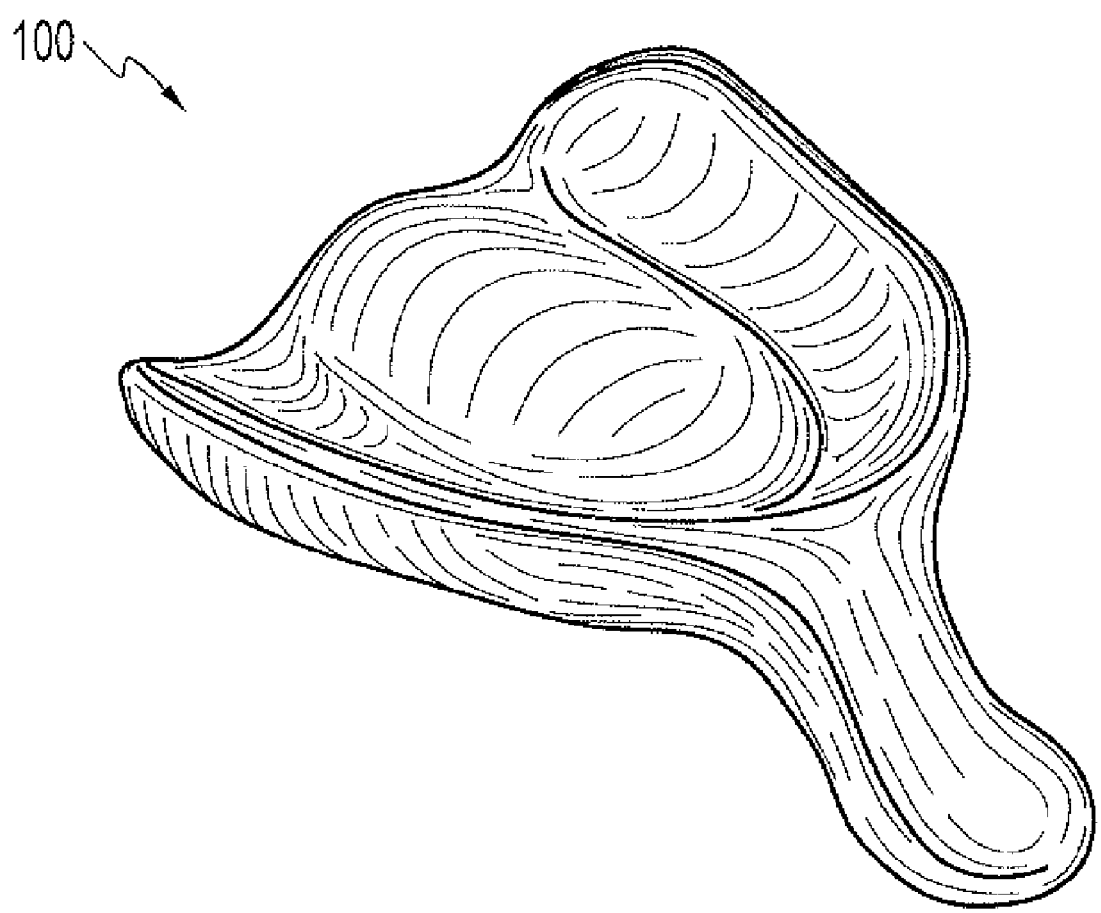
FIG. 7 illustrates a perspective view of the maxilla tray 100 shown in FIG. 1.

Referring to FIG. 7, a perspective view of the maxilla tray 100 is shown.

Figure 8:
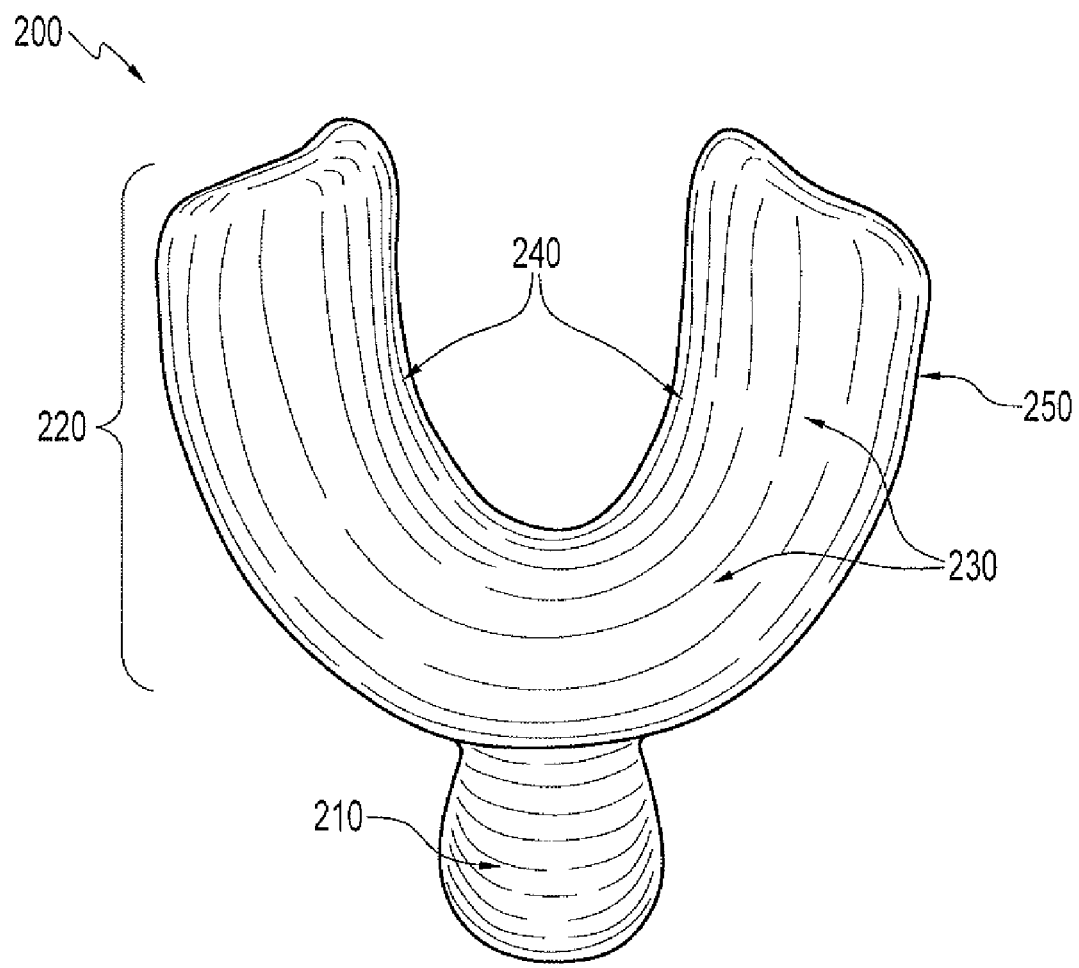
FIG. 8 illustrates a top view of a mandible tray in accordance with features of the present invention.

Referring to FIG. 8, a bottom view of a mandible tray 200 in accordance with features of the present invention is shown. The tray 200 is shown with a handle 210 and a main body 220 that is formed as an arch or as the shape of a horse hoof. The main body 220 is further formed by person's teeth and alveolar bones during use when they are received within the trench 230, which includes interior and exterior walls, labeled 240 and 250 respectively. The tray 200 is made of a single, uniform thermoplastic resin-based material. The resin is comprised of polycaprolactone resin, styrene resin and dental modeling compound. The proportions can vary for specific uses but are roughly 50% polycaprolactone/styrene resin and 50% dental modeling compound.

Figure 9:
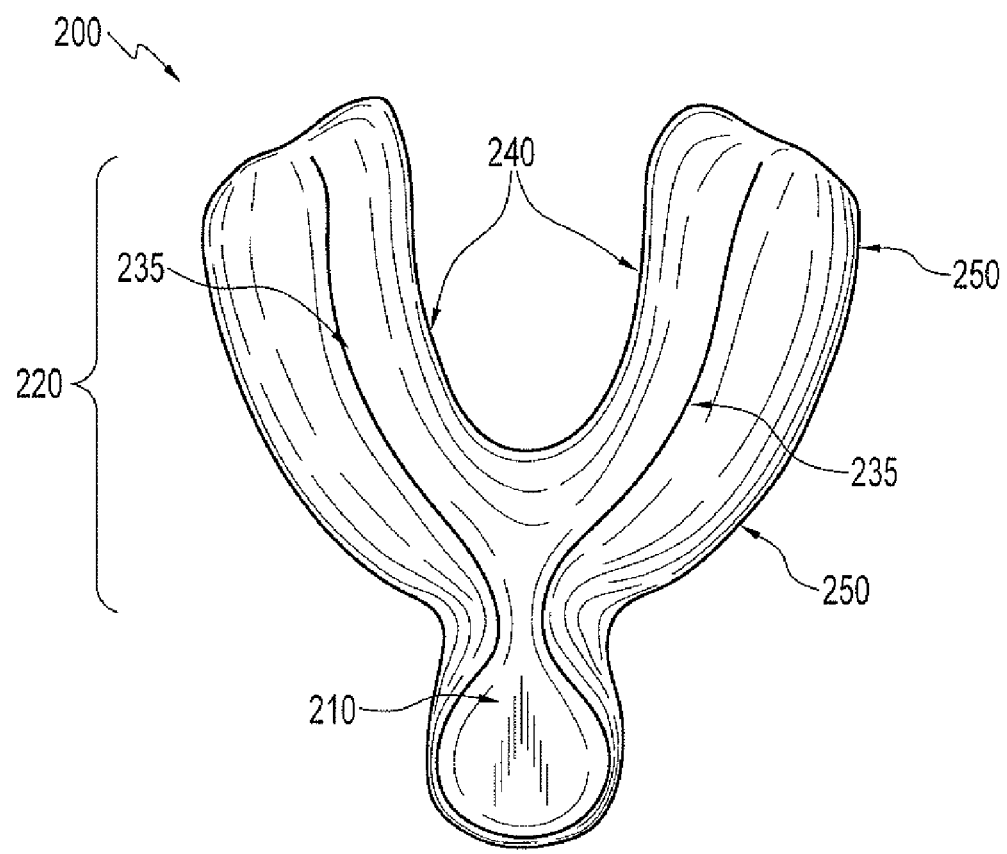
FIG. 9 illustrates a bottom view of the mandible tray shown in FIG. 8.

Referring to FIG. 9, a top view of the mandible tray 200. The handle 210 is also shown in FIG. 9. Also shown in FIG. 9 is the outer surface detail of the trench wherein a ridgeline 235 generally follows the shape of a horseshoe along the bottom surface, opposite the trench 230 shown in FIG. 8.

Figure 10:
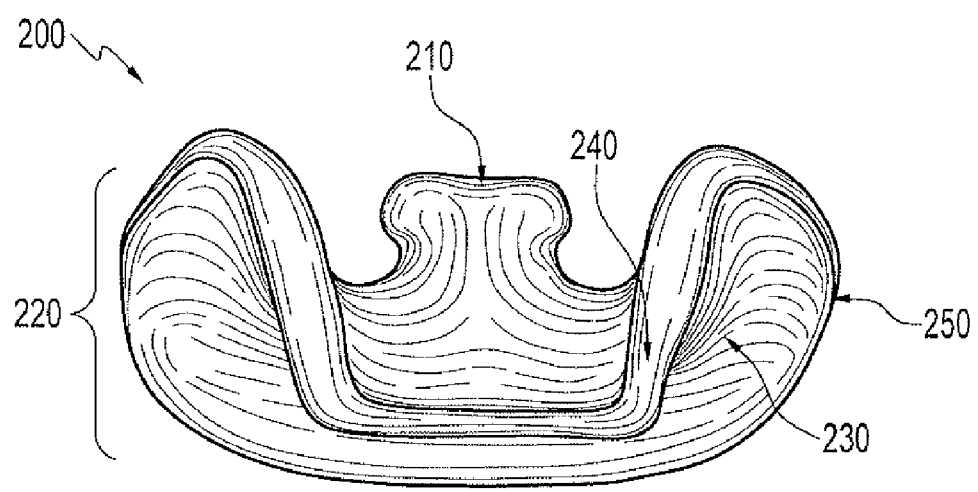
FIG. 10 illustrates a rear view of the mandible tray shown in FIG. 8, with more detail of a trench as formed by interior and exterior walls.

Referring to FIG. 10, a back view of the mandible tray 200 is shown with more detail of the trench 230 as formed by the interior wall 240 and exterior wall 250. The handle 210 is also shown in FIG. 10 in raised relation to the main body 220.

Figure 11:
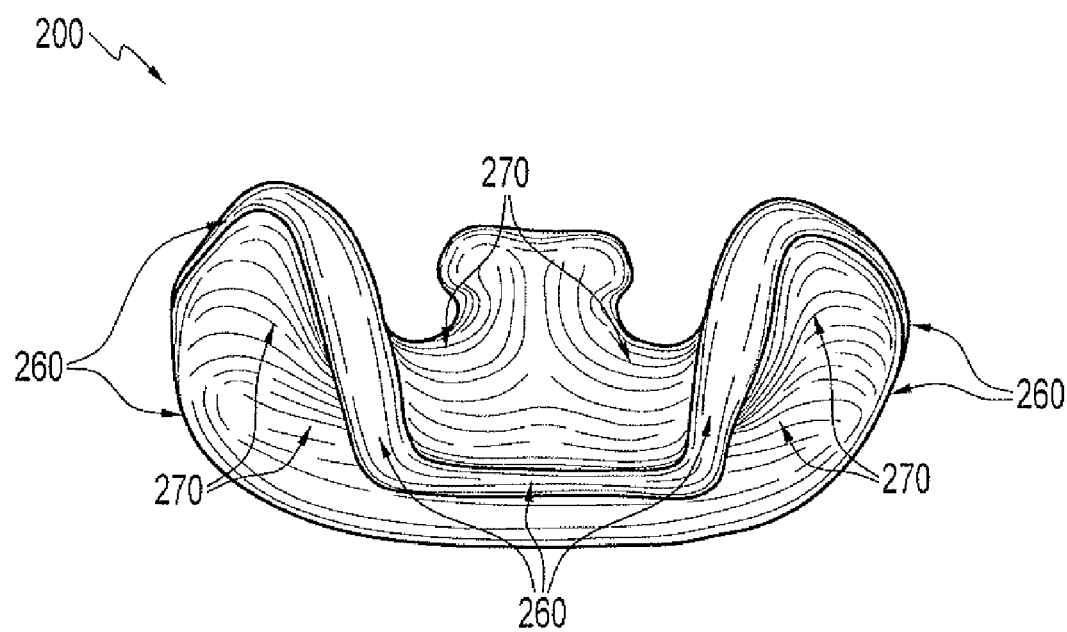
FIG. 11 illustrates areas of variable thickness along the trench and wall areas of the mandible tray from FIG. 8, which enable tray manipulation.

Referring to FIG. 11, thick and thin walled areas of the mandible tray 200 are shown. FIG. 11 illustrates the various thicknesses embodied within the tray's main body 220 that enable ease of tray manipulation (thin areas 260) while overall tray integrity can be maintained (thick areas 270). The thick regions 270 enable technicians/dentists to maintain the trays integrity, including its basic horseshoe shape. The thinner regions 260 are located in areas along the tray that traditionally cause problems during use, including patient discomfort, difficulty achieving a snug fit of the tray with the patients teeth, gums and mouth.

Figure 12:
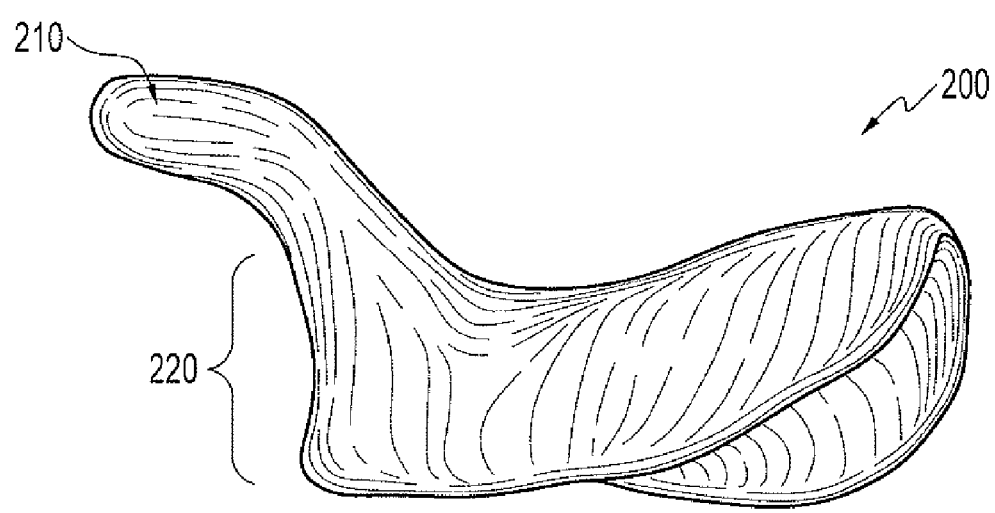
FIG. 12 illustrates a side view of the mandible tray shown in FIG. 8.

Referring to FIG. 12, a side view of the mandible tray 200 is shown. The main body 210 and handle 220 are shown. The side view of the main body 210 also shows the interior wall 230 and exterior wall 240.

Figure 13:
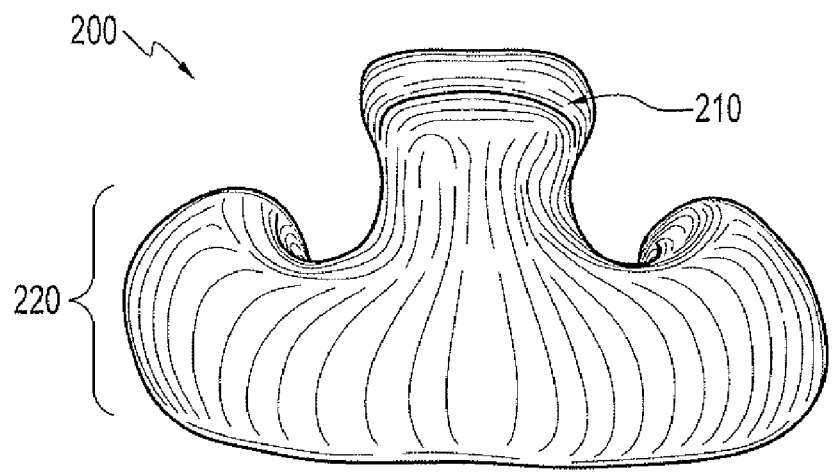
FIG. 13 illustrates a front view of the mandible tray shown in FIG. 8.

Referring to FIG. 13, a front view of the mandible tray 200 is shown. The main body 210 and handle 220 are also shown.

Figure 14:
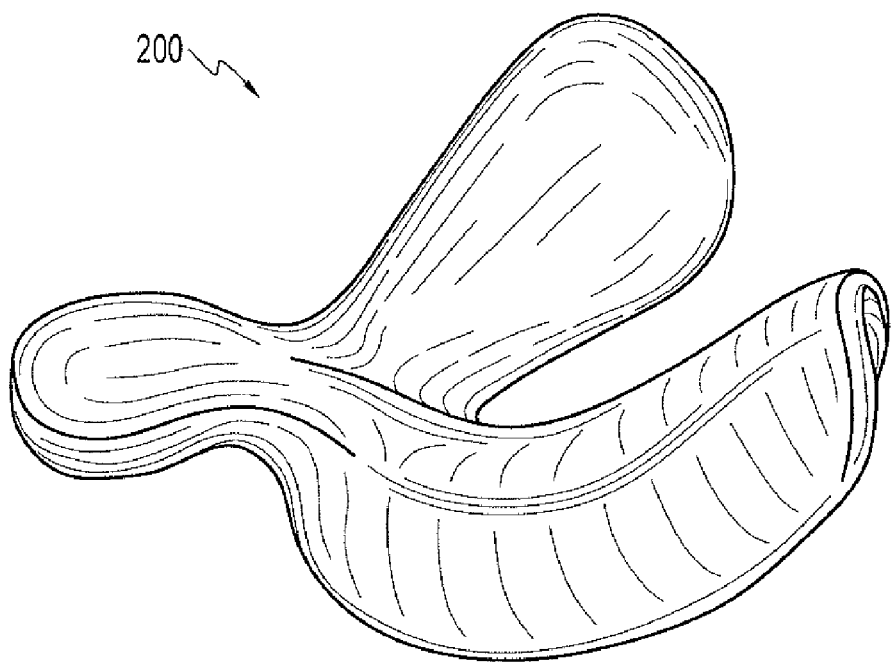
FIG. 14 illustrates a perspective view of the mandible tray shown in FIG. 8.

Referring to FIG. 14, a perspective view of the mandible tray 200 is shown.

Both the maxillary and mandible trays are stiff and inflexible at body temperature. The resin becomes pliable after placing the tray in at least 140 degrees F. water for 30 to 45 seconds. Over heating the trays, however, can cause the integrity of the tray to breakdown. Therefore, the ideal range for heating trays is from 140 degrees to 160 degrees Fahrenheit, with a target temperature of 150 degrees Fahrenheit. Overheating can also be prevented by removing the tray from the water before the entire tray softens and it is controlled by the second design element. The trays are manufactured with varying cross-sections. Thinner areas soften first and thicker areas soften last. Areas that should be soft and flexible during the impression tray making process such as the flanges of the tray are thinner than the core of the tray that must stay rigid and intact. However, even the thin areas of the tray vary in their thickness. This allows the trays to soften in sections allowing even more control of the impression making process. The clinician has a great deal of control of the tray's flexibility—the part of the tray one desires to manipulate is simply heated and becomes soft while the other parts of the tray will remain rigid.

During the basic process of developing a patient's impression, a warmed tray is first placed in the patient's mouth. The tray is adapted to the unique anatomy of the patient's mouth and the tray is removed. After cooling in cold water, the tray is modified by adding or removing material as needed. The tray is then warmed again and border molded. The tray is once again removed and cooled. The final impression is then made using any impression material chosen by the clinician.

Heating and cooling is a basic technique required to use the trays effectively. This accomplishes two things—cooling the tray sets the position of the tray material and two—cooling the tray prevents the tray core from softening and distorting the trays shape. Since the tray is mostly made of a single, uniform thermoplastic material, care must be taken to heat and soften only the areas that are to be manipulated. This is accomplished by selective heating the tray. Heated regions of the tray are visually indicated by change in color of thermochromic pigment when used with the tray's thermoplastic material. The tray is partially submerged into 150 degree F. (or 140 to 160 F.) water for 30 to 45 seconds. This softens the tray flanges without softening the rest of the tray. If the tray is softened for less time or cooled off with water, the material will become less pliable. If the tray is heated longer or in hotter water, the material will become softer. Of course overheating will cause the tray to break down and become unwieldy. This can be reversed by placing the tray in cold water. Cooling the tray causes the tray to quickly harden. Room temperature water will do but chilled or ice water works faster.

Material can be added to trays to extend the flanges, add a posterior palatal seal, fill the palate, if necessary, or create the foundation for an obturators bulb. The technique is simple. Warm a room temperature or cold tray for a few seconds in at least 140 degree F. water in order to create a soft skin on the surface. Squeeze the molten excess material onto the tray with some pressure. This effectively bonds the added material to the tray. You can't bond softened material to a cold tray. Although this may occasionally be used to your advantage, it usually causes problems somewhere down the line.

There are only a few tools required to use the trays effectively—the first being the trays themselves. Each tray can be added to using extra tray material to enlarge or modify the tray as needed. The tray and material are placed in hot water of about 150 degrees F. Once the tray and material become soft, the extra material is placed as needed along the tray. The tray is then placed into chilled or ice water, which will cool the tray quicker. A sharp blade (e.g., such as a bard parker blade) is used to trim excess material. A tray can also be reduced. Large sections of tray can effectively be removed with cutters or nippers. Once modifications are made to the tray, a rotating nylon wheel can be used to thin the tray flanges. Since these cuts can be irritating to the patients' oral mucosa, it's usually a good idea to smooth these cut surfaces by heating the tray for a few moments in warm water and then polishing the surface with a gloved finger.

The resin can be perforated without compromising the structural integrity of the tray. The insertion of perforations or holes within the trays is helpful for open tray techniques for implant impression making.

Mistakes to the trays can be corrected. The tray can be shaped by simply recontouring the warm material with a gloved finger or fingers. After recontouring, the repaired tray can be chilled in cold water.

The thickness of the tray flanges can be important. A nylon brush can be used to thin cold flange material where necessary and to recontour other areas of the tray if desired. The surfaces roughened by the wheel can be polished by warming the tray surface and polishing the roughed edges with a gloved hand.

Most impression making techniques required some tray relief to allow for the passive placement of tray material. The simplest way to create relief is to recontour the warmed tray material with gloved fingers. This allows for placing relief in the intended places. Using a second technique, relief can be created using wax. Wax can be placed in the tray in areas that relief is planned. The waxed tray is first placed in the mouth and manipulated. The wax is then removed after the tray is cooled in chilled water. The resultant space will be filled during the final impression making procedure.

The completed tray should be placed in the patient's mouth prior to making the final impression. Any shrinkage of the material can be adjusted by heating the tray for a few seconds and finessing the shape in the patients' mouth. The final impression can be made using any tradition impression-making medium. Vent holes can also be placed in the tray if desired.

Figure 15:
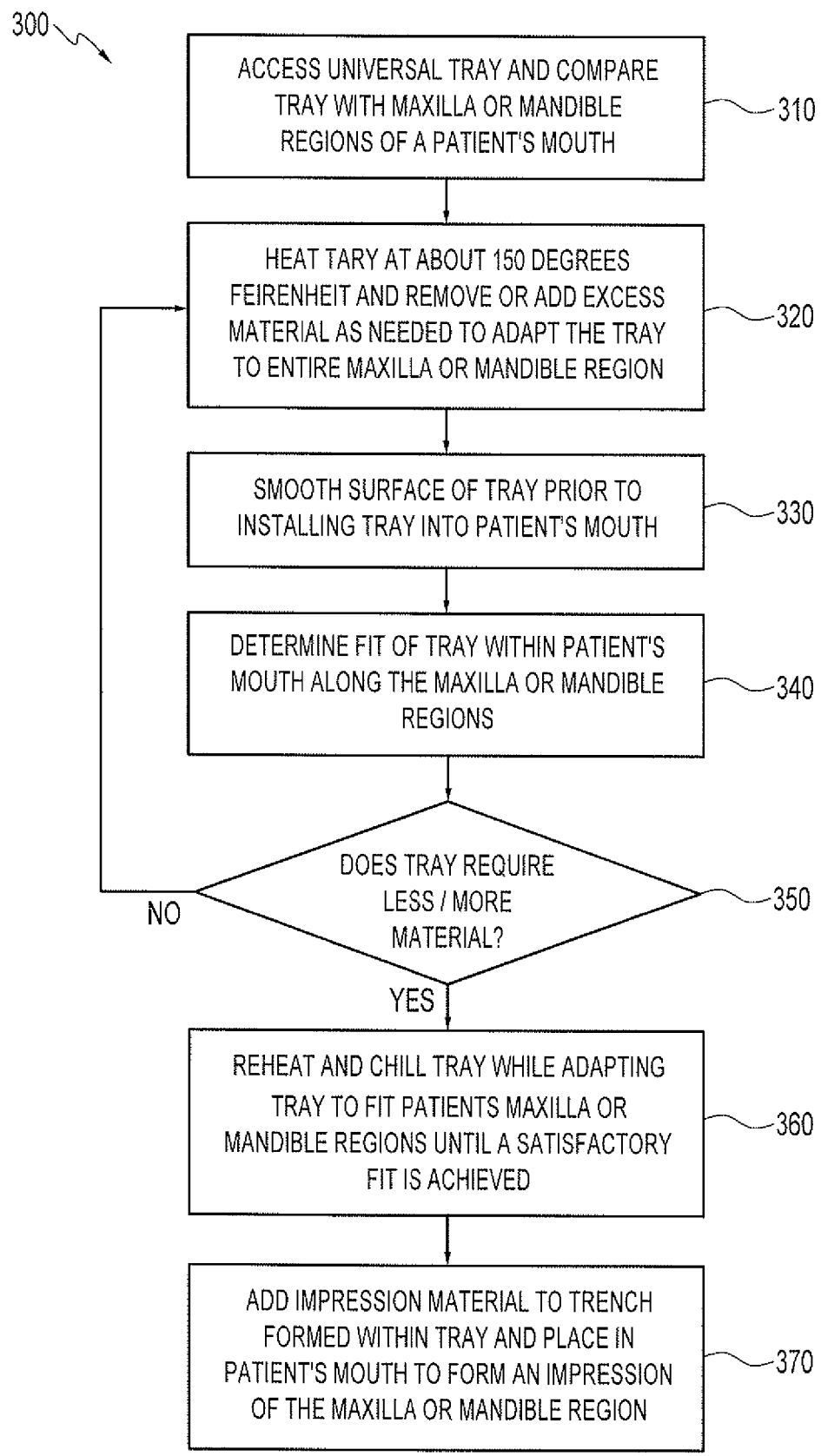
FIG. 15 illustrates a flow diagram of a process of using a tray in accordance with features of the present invention.

Referring to FIG. 15, a flow diagram 300 of the general process of using the universal tray described herein is shown. Referring to Block 310, a universal tray is accessed from clinic stock and is compared with the maxilla or mandible regions of a patient's mouth. After the comparison, and as shown in Block 320, the tray is heated at about 150 degrees Fahrenheit so that excess material can be added or removed to the tray as needed to adapt it to the entire maxilla or mandible region of the patient's mouth. As shown in block 330, surfaces of the tray are smoothed out after material is added or removed prior to reinstalling the tray into the patient's mouth for further adjustment. As shown at block 340, the clinician will determine if the adjusted tray fits within the patient's mouth along the maxilla or mandible regions. As shown in decision block 350, the clinician decides whether the tray requires more or less material. If the tray requires the addition or removal of material, the process returns to block 320 where the steps for blocks 320 through 350 are repeated. If no further material alterations are required, the clinician move on to block 360 wherein the tray is reheated and chilled during manipulation and while the tray is being adapted to the patients maxilla or mandible regions. The process is repeated until a satisfactory fit is achieved. At block 370, impression material is added to a satisfactory fitting tray, and the tray placed in the patient's mouth so that an impression of the maxilla or mandible regions can be achieved.

Figure 16:
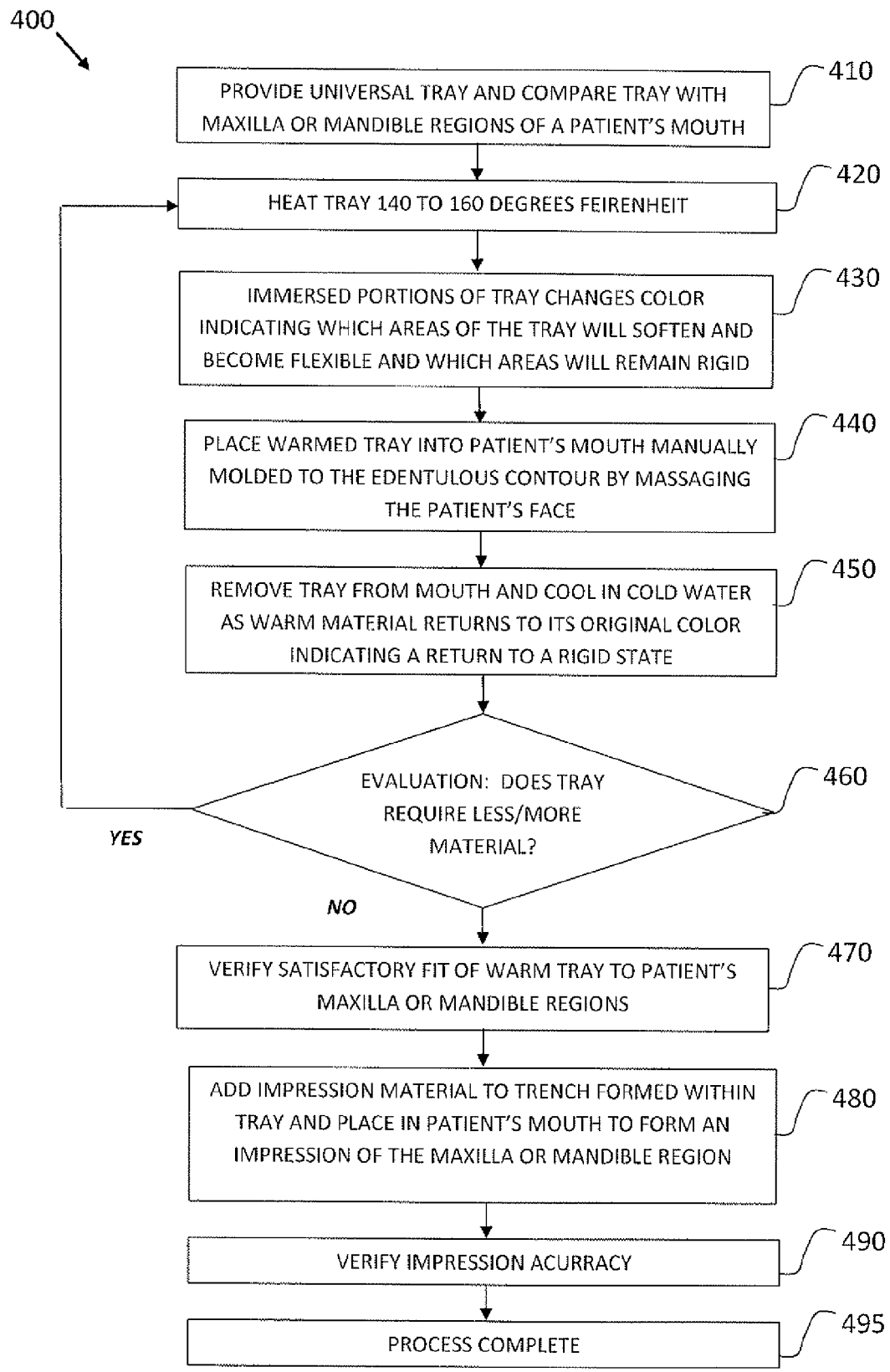
FIG. 16 illustrates a flow diagram of a process of using a tray in accordance with features of the present invention.

Referring to FIG. 16, another flow diagram 400 of a process of using a universal tray including thermochromic material is shown. The method of use is as follows: at least one of two different edentulous trays can be provided and are compared by a dental professional with the maxilla or mandible regions of a patient's mouth, as shown in block 410. The tray is heated by partially immersing the tray body into 140 to 160 degree Fahrenheit water as shown in block 420. The immersed material changes color (typically from a blue to tan color) indicating which areas of the tray will soften and become flexible and which areas will remain rigid, as shown in block 430. This selective heating of the tray body will allow the tray body to retain its shape during the impression making process. After the tray is warmed, it is place on the patient's edentulous arch and manually molded to the edentulous contour by massaging the patient's face, as shown in block 440. This process adapts the softened material to the ridge and begins to customize the tray. Then as shown in block 450, the tray is removed from the mouth and cooled in cold water. The warm material returns to its original color (i.e., blue) indicating a return to a rigid state. The tray is evaluated by the dental practitioner and further modified if needed, which is shown in block 460. Modifications could include shortening the tray's contours with a knife or scissor, adding extra material to the original tray form, smoothing sharp edges, or removing excess material with a bur. All these modifications require heating or cooling the material and is facilitated the color changing ability of the tray material; therefore, the steps shown in blocks 420 through 460 can be repeated as necessary, which is shown in decision block 460. The tray is again warmed in water and placed in the patient's mouth. This step confirms the fit of the tray, as shown in block 470. The tray is then removed from the mouth and cooled if necessary. As shown in block 480, an accurate final impression material is placed in the tray and the tray is reinserted in the patient's mouth. The tray and cured impression material is removed from the mouth and evaluated for accuracy and detail as shown in block 490. The impression making process is then completed as shown in block 495.

The invention claimed is:
1. A universal edentulous impression tray, comprising:
a main body comprising a trench, an interior wall and an exterior wall;
said interior wall comprising a varying thickness from a top of said interior wall to a bottom of said interior wall;
said exterior wall comprising a varying thickness from a top of said exterior wall to a bottom of said exterior wall;

a bottom surface of said trench comprising a greater thickness than said interior wall thicknesses and said exterior wall thicknesses;

a handle integrated with a front of said main body, said handle comprising a greater thickness than said interior wall thicknesses and said exterior wall thicknesses;

said universal edentulous impression tray comprising a single uniform unit made of a thermoplastic resin that is pliable while retaining its shape at or above a predetermined temperature; and said tray reshapable and said thermoplastic resin added to or removed from said tray when said thermoplastic resin is at or above said predetermined temperature, and said tray maniputable allowing a clinician the ability to manipulate said tray in a clinical situation.

2. The invention of claim 1 wherein said thermoplastic resin portion of said tray further comprises polycaprolactone resin, styrene resin and dental modeling compound.

3. The invention of claim 1 wherein said predetermined temperature is between 140 degrees Fahrenheit and 160 degrees Fahrenheit.

4. The invention of claim 1 further comprising a thermochromic pigment incorporated into said thermoplastic resin enabling portions of said tray to change color upon reaching said predetermined temperature.

5. A universal edentulous impression tray comprising:
a main body comprising:
  a base portion,
  an interior wall and an exterior wall separated and connected to said base portion and forming a trench therebetween, and
  a handle integrated with said main body along said exterior wall,
  said base portion and said handle comprising thicker portions as compared to said interior wall thicknesses and said exterior wall thicknesses,
  said interior wall comprising a varying thickness from a top of said interior wall to a bottom of said interior wall;
  said exterior wall comprising a varying thickness from a top of said exterior wall to a bottom of said exterior wall;
  said main body shaped to fit within a mouth and surround teeth associated with at least one of the maxilla or mandible regions of the mouth,
  said tray comprising a single uniform unit made of a thermoplastic resin that is pliable while retaining its shape at or above a predetermined temperature;
  said tray is adapted to be selectively reshaped, shortened or lengthened by a clinician after it has reached said predetermined temperature, and
  said interior and exterior walls are pliable at said predetermined temperature while said trench and said handle maintain their integrity because of their increased thickness relative to said interior and exterior walls.

6. The invention of claim 5 wherein said thermoplastic resin further comprises polycaprolactone/styrene resin and dental modeling compound.

7. The invention of claim 5 wherein said main body is manipulatable by removing or adding thermoplastic material when said tray and said thermoplastic material is warmed to at least 140 degrees Fahrenheit.

8. The invention of claim 5 further comprising a thermochromic pigment incorporated into said thermoplastic resin allowing portions of said tray to change color at said predetermined temperature to indicate pliable areas.

9. The invention of claim 5 wherein said main body is manipulatable by removing or adding thermoplastic material when said tray and said thermoplastic material is warmed to about 150 degrees Fahrenheit.

10. The invention of claim 8 wherein said thermochromic pigment portion of said tray is less than 5% of said tray's overall material composition.

* * * * *